ically a methyl glucoside polyol to the composition in an amount sufficient to reduce alcohol solvent pungency and improve fragrance intensity and fixation.
United States Patent [19]
Seldner

[11] 4,264,478
[45] Apr. 28, 1981

[54] POLYOL FRAGRANCE FIXATIVES

[75] Inventor: Abraham Seldner, Princeton, N.J.

[73] Assignee: Amerchol Corporation, Edison, N.J.

[21] Appl. No.: 106,791

[22] Filed: Dec. 26, 1979

Related U.S. Application Data

[63] Continuation-in-part of Ser. No. 955,672, Oct. 30, 1978, abandoned.

[51] Int. Cl.³ .............................................. C11B 9/40
[52] U.S. Cl. .............................................. 252/522 R
[58] Field of Search ....................... 252/522 A, 522 R; 536/4, 120

[56] References Cited

U.S. PATENT DOCUMENTS

| | | | |
|---|---|---|---|
| 2,556,410 | 9/1951 | Griffin | 252/522 A |
| 2,996,551 | 8/1961 | De Groote et al. | 536/120 |
| 3,042,666 | 7/1962 | Gentles | 536/120 |
| 3,357,970 | 12/1967 | Wyatt | 536/120 |
| 3,370,056 | 2/1968 | Yotsuzuka | 536/4 |
| 3,441,616 | 4/1969 | Pizzini et al. | 536/120 |
| 3,445,525 | 5/1969 | Bormann et al. | 536/4 |
| 4,016,098 | 5/1977 | Saeki et al. | 252/522 A |
| 4,128,507 | 12/1978 | Mitzner | 252/522 A |
| 4,217,445 | 8/1980 | Nikolaiski | 536/4 |

*Primary Examiner*—Veronica O'Keefe

[57] ABSTRACT

Colognes, toilet waters, after-bath splashes and other fragranced compositions are given improved fragrance fixation by the addition of methyl glucoside polyols. When these essentially odorless polyols are added to such compositions in amounts from about 0.5% to about 5% by weight based on the total alcoholic, aqueous or hydroalcoholic content of said compositions, lasting power and intensity of the fragrance are improved and alcohol solvent pungency is reduced. The improvement in fragrance intensity also allows the fragrance formulator to reduce the quantity of fragrance oil in a given composition. Virtually any fragrance formulation can be improved in accordance with the present invention.

3 Claims, No Drawings

POLYOL FRAGRANCE FIXATIVES

This application is a continuation-in-part of application Ser. No. 955,672, filed Oct. 30, 1978 now abandoned.

BACKGROUND OF THE INVENTION

1. Field of the Invention

This invention relates to methods and compounds useful in fragrance fixation and particularly relates to use of methyl glucoside polyols in fragrance formulations.

2. The Prior Art

Fragrance formulation is an art in which the senses of the skilled perfumer are more important than mere chemical analysis. A fragrance results from a variety of components in a fragranced composition. Ordinarily, fragrances are created by blending materials comprising odoriferous essential oils, extracts from woods, gums, flowers and other botanicals, resins, animal secretions, and synthetic aromatic materials. These materials are skillfully blended in order to achieve what are known as a "top note", a "middle note," and an "end note." The first is the refreshing quality sensed upon application. The last is the essence of the fragrance which stays with the wearer for a long time. The middle note is the perceived quality that bridges from top to end note.

In the creation of fragrances, certain materials are generally selected for their use as fragrance fixatives. These are substances which amplify the intensity and lasting qualities of aromatic components of a fragrance. (The term "aromatic" as used in this specification is defined in the perfumers' sense of "odorous substances" rather than in the chemical sense.) A fragrance fixative has principal activity with respect to the lasting quality and the end note of the fragrance.

Many materials are available to the perfumer as fixatives, Among these are the following:

1. Floral and botanical absolutes, concretes and resinoids.
2. Animal secretions and extracts.
3. Macrocyclic musks.
4. Nitro musks.

Floral and botanical absolutes, concretes and resinoids are produced by extraction with volatile and nonvolatile solvents or other menstruums. Essential oils (volatile oils) are found in plants and obtained by steam distillation or other methods. Generally, essential oils are defined as the more-or-less volatile material isolated from an odorous plant of a single botanical species by a physical process. Flower oils, concretes and resinoids (oleo resins) being only partially volatile are therefore only partly essential oils. The method of their preparation often imparts fixative properties.

Animal secretions and extracts used for fixatives generally include musks derived from glands of the male musk deer (natural musk or Musk Tonquin), the civet cat (civet) or the beaver (castoreum) as well as ambergris which is not a gland secretion but an accumulated material in the whale.

Macrocyclic musks are synthetic compounds like the macrocyclic ketones or lactones and also include indans and tetralins, derivatives of hydrindacene, isochroman, naphthindan, and coumarin.

Nitro musks include various nitro benzene compounds.

In addition to the foregoing materials, some references in the art to other synthetic materials having no odor of their own as fragrance fixatives have been made to ethylphthalate and to benzyl benzoate. Actually, these materials do little to strengthen and prolong the fragrance of fragranced materials, but they are useful as low volatility solvents for a broad range of fragrance materials.

It is well known that prior art fragrance fixatives can distort the nature or character of the fragrance being fixed. This problem is overcome in accordance with the present invention wherein essentially odorless methyl glucoside polyols are used as fragrance fixatives.

SUMMARY OF THE INVENTION

The present invention relates to the discovery that certain methyl glucoside polyols are useful as fragrance fixatives. More specifically, these compounds include alkoxylated methyl glucoside and particularly ethoxylated and propoxylated methyl glucoside.

Effective amounts of these materials for fragrance fixation are in the range from about 0.5% to about 5.0% by weight based on the total alcoholic, aqueous or hydroalcoholic content of the fragranced product.

It has also been found that fragrance products incorporating methyl glucoside polyols in accordance with this specification do not require as high a concentration of aromatic materials as is required in similar fragranced products which do not incorporate said polyols.

Another benefit achieved through the addition of methyl glucoside polyols to fragranced products is a reduction of pungent solvent odors caused by the alcohol solvent commonly used in such products.

The fixative system described in this specification is useful in fragrance systems such as perfumes, colognes, after-bath splashes, aftershaves, perfumed powders, perfumed p-dichlorobenzene, soaps, creams, lotions, and virtually every other system which can be fragranced.

DETAILED DESCRIPTION OF THE INVENTION

The use of methyl glucoside polyols as a fixative in fragranced products produces dramatic increases in the lasting power of the fragrance. The fixative, however, does not change the nature or character of the fragrance being fixed in any other significant fashion. Thus the lasting power of the fragrance is increased without distortion. These properties are not available in other materials presently in use.

An additional advantage is that the methyl glucoside polyols of this invention are soluble in water, alcohol and water-alcohol systems. Most fixatives of the prior art are insoluble in water.

The methyl glucoside polyols used in accordance with the present invention can be derived from glucose. In a first step, methyl glucoside is prepared from glucose in accordance with the following generalized reaction scheme:

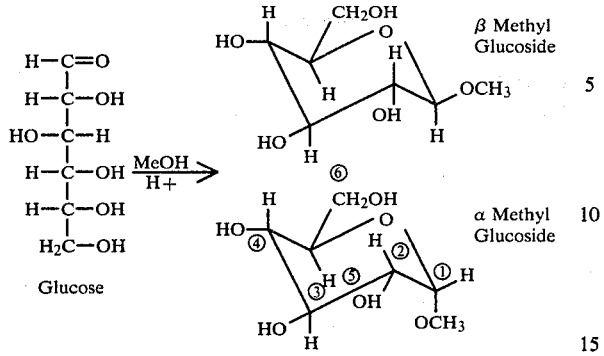

Glucose — β Methyl Glucoside / α Methyl Glucoside

The mixture of alpha and beta methyl glucoside shown in the above reaction is generally in a ratio of about 2:1. The molecule has the pyranoside form (ring consisting of 5 carbons and 1 oxygen) and is classified as a cyclic or "internal" full acetal. Methyl glucoside has four hydroxyl groups which are available for reaction to form various derivatives. The reaction is favored to take place on the primary hydroxyl (#6 carbon) with the hydroxyl group adjacent to the methoxy group (#2 carbon) being the next most reactive. The stability of the ring structure and the reactivity of the hydroxyl groups allow for the preparation of various derivatives without the formation of degradation products that would be expected to form if glucose were subjected to the same reactions.

Methyl glucoside can be reacted with alkylene oxides to produce methyl glucoside polyols. A typical method used, is to react the aklylene oxide with methyl glucoside in the presence of an alkaline catalyst (such as potassium hydroxide) at a temperature of 140°–160° C. Since the alkylene oxide generally has a boiling point below the reaction temperature, a sealed vessel is used and the reaction is carried out at elevated pressure. The reaction is favored to take place on the primary hydroxyl (#6 carbon) with the hydroxyl group adjacent to the methoxy group (#2 carbon) being the next most reactive, as stated above. After the reaction is complete, the akaline catalyst is neutralized with an acid.

Methyl glucoside polyols are commercially available from Amerchol Corporation, Talmadge Road, Edison, New Jersey under the trademark GLUCAM ® methyl glucoside polyol. GLUCAM E-10 and GLUCAM E-20 are the 10 and 20 mole ethoxylates, respectively. GLUCAM P-10 and GLUCAM P-20 are the 10 and 20 mole propoxylates, respectively. GLUCAM P-20 is, for example, prepared by reacting 20 moles of propylene oxide with 1 mole of methyl glucoside to form a composition having the formula:

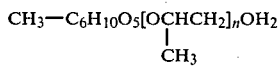

where n has an average value of 20.

The methyl glucoside polyols of the present invention are added to fragranced compositions in amounts from about 0.5% to about 5% by weight based upon total alcoholic, aqueous or hydroalcoholic content of said composition to produce an acceptable fragrance fixation effect. The preferred range is from about 1.0% to about 2.5%. Excess methyl glucoside polyol may be added to fragranced systems such as colognes and toilet waters to improve the feel of such material and the rub-in of the finished product on the skin. For this purpose, from about 2% to about 15% methyl glucoside polyol is useful. In such uses, the methyl glucoside polyol can also replace other polyols in the system such as glycerine, sorbitol or propylene glycol in alcoholic and hydroalcoholic products while at the same time accomplishing the fragrance fixation which the traditional polyols do not exhibit.

The methyl glucoside polyols are true fragrance fixatives in that they increase the lasting power of the fragrance involved. Moreover, they make it possible to get the same fragrance sensation using less fragrance material. They have a further advantage in that they reduce the pungent solvent odor present in alcoholic and other fragrance solutions.

The following examples are provided to further illustrate the invention. Unless otherwise specified all percentages are weight/weight.

EXAMPLE 1—Perfume

|  | 1-A | 1-B |
|---|---|---|
| Aldehydic - Floral Perfume Oil | 12.0% | 12.0% |
| 20 mole propoxylate of methyl glucoside | 0.0 | 2.5 |
| Alcohol | 88.0 | 85.5 |

In panel studies, in periods ranging from one to ninety-six hours, 97% of the panelists determined longer lasting properties on skin in the formulation with 2.5% 20 mole propoxylate of methyl glucoside (1-B) compared to the formulation without this methyl glucoside polyol (1-A). On tests on perfume blotters, 94% of the panelists made the same choice.

EXAMPLE 2—After-Bath Splash

|  | 2-A | 2-B |
|---|---|---|
| Citrus-Lavender-Fougere Perfume Oil | 2.2% | 2.2% |
| 20 mole propoxylate of methyl glucoside | 0.0 | 2.0 |
| Alcohol | 76.0 | 74.0 |
| Water | 21.8 | 21.8 |

In panel studies, 93% of the panelists preferred the lasting properties on skin of the 2-B formulation over the 2-A formulation. On perfume blotters of the formulations, 90% of the panelists preferred the 2-B formulation to the 2-A formulation.

EXAMPLE 3—Eau de Toilet

|  | 3-A | 3-B |
|---|---|---|
| Herbal - Woody Perfume Oil | 8.0 | 8.0 |
| 20 mole propoxylate of methyl glucoside | 0.0 | 2.0 |
| Alcohol | 86.0 | 84.0 |
| Water | 6.0 | 6.0 |

In panel studies, 95% of the panelists preferred the 20 mole proproxylate of methyl glucoside treated product (3-B) on skin. On perfume blotters, 89% preferred the same product.

EXAMPLE 4—Cologne

|  | 4-A | 4-B |
|---|---|---|
| Citrus - Floral Perfume Oil | 5.0% | 5.0% |
| 20 mole propoxylate of methyl glucoside | 0.0 | 1.0 |
| Alcohol | 75.0 | 74.0 |
| Water | 20.0 | 20.0 |

In panel studies, 93% of the panelists preferred 20 mole propoxylate of methyl glucoside treated product (4-B) on skin. On perfume blotters, 86% preferred the same product.

EXAMPLE 5—Aftershave Lotion

|  | 5-A | 5-B |
|---|---|---|
| Spanish Leather Perfume Oil | 0.6% | 0.6% |
| 10 mole ethoxylate of methyl glucoside | 0.0 | 3.0 |
| Alcohol | 63.0 | 60.0 |
| Water | 36.4 | 36.4 |

In panel studies over periods ranging from one to twenty-four hours, 89% of the panelists determined longer lasting properties on skin for the product with 10 mole ethoxylate of methyl glucoside (5-B) compared to the product without this methyl glucoside polyol (5-A). On perfume blotters, 84% of the panelists preferred the lasting quality of the (5-B) product.

EXAMPLE 6—Dusting Powder

|  | 6-A | 6-B |
|---|---|---|
| Floral Musk - Woody Perfume Oil | 1.5% | 1.5% |
| 10 mole propoxylate of methyl glucoside | 0.0 | 1.5 |
| Magnesium carbonate | 3.0 | 3.0 |
| Talc | 95.5 | 94.0 |

In panel studies, 86% of the panelists found longer lasting properties in skin tests in the formulation containing 10 mole propoxylate of methyl glucoside (6-B) as compared to the other formulation.

EXAMPLE 7—Hand Cream

|  | 7-A | 7-B |
|---|---|---|
| Methyl glucoside sesquistearate | 0.8% | 0.8% |
| Acetylated lanolin | 2.0 | 2.0 |
| Cetyl alcohol | 2.0 | 2.0 |
| Mineral Oil | 6.0 | 6.0 |
| Stearic Acid | 2.0 | 2.0 |
| 20 mole ethoxylate of methyl glucoside sesquistearate | 1.2 | 1.2 |
| Glycerine | 5.0 | 0.0 |
| 20 mole ethoxylate of methyl glucoside | 0.0 | 5.0 |
| Albagel | 1.5 | 1.5 |
| Fluoral Perfume Oil | 0.5 | 0.5 |
| Water | 79.0 | 79.0 |

Over a period of one to four hours, the cream with 20 mole ethyloxylate of methyl glucoside (7-B) was judged by 82% of the panelists to exhibit greater intensity and longer lasting power than the same cream without the methyl glucoside polyol.

EXAMPLE 8—Deodorant Blocks

|  | 8-A | 8-B |
|---|---|---|
| Paradichlorobenzene | 99.5% | 97.5% |
| 20 mole propoxylate of methyl glucoside | 0.0 | 2.0 |
| Floral Spice Perfume Oil | 0.5 | 0.5 |

In use in urinals over one to four week periods, blocks containing 20 mole propoxylate of methyl glucoside (8-B) were judged by 87% of the panelists to emit a higher intensity of odor than blocks without the methyl glucoside polyol.

EXAMPLE 9—Soap Bars

|  | 9-A | 9-B |
|---|---|---|
| Soap stock | 98.5% | 96.5% |
| 20 mole propyxylate of methyl glucoside | 0.0 | 2.0 |
| Lilac Perfume Oil | 1.5 | 1.5 |

In wash use tests, 94% of the panelists judged the intensity of fragrance in soap bars containing 20 mole propoxylate of methyl glucoside (9-B) to be greater than that in bars without the methyl glucoside polyol.

EXAMPLE 10—Reduction of Perfume Oil Concentration in After Bath Splashes

|  | 10-A | 10-B |
|---|---|---|
| Citrus-Lavender-Fougere Perfume Oil | 2.2 | 1.7% |
| 20 mole propoxylate of methyl glucoside | — | 2.0 |
| Alcohol | 76.0 | 74.5 |
| Water | 21.8 | 21.8 |

In panel tests on skin and perfume blotters, 43% of the panelists judged Formula 10-B to be stronger in fragrance than Formula 10-A. The remaining 75% judged 10-A and 10-B to be equal. Use of such reduced concentration of perfume oils without adverse effect on perception of odor will provide significant savings in material costs.

EXAMPLE 11—Reduction of Perfume Oil Concentration in Perfume

|  | 11-A | 11-B |
|---|---|---|
| Aldehydic-Floral Perfume Oil | 12.0% | 10.0% |
| 20 mole propoxylate of methyl glucoside | — | 2.0 |
| Alcohol | 88.0 | 88.0 |

In panel tests, 43% of the panelists judged Formula 11-B with 20 mole propoxylate of methyl glucoside to be stronger than Formula 11-A without the methyl glucoside polyol; 28.5% found no difference and 28.5% judged 11-A to be stronger. Thus 71.5% of the panelists accepted the reduced perfume oil concentration as equal or better with possible attendant major cost savings. Tests were run on skin and blotters.

EXAMPLE 12—Reduction of Perfume Oil Concentration in Colognes

|  | 12-A | 12-B |
|---|---|---|
| Citrus-Floral Perfume Oil | 5.0% | 4.0% |
| 20 mole propoxylate of methyl glucoside | — | 2.0 |
| Alcohol | 75.0 | 74.0 |
| Water | 20.0 | 20.0 |

In panel tests 28.5% of the panelists judged Formula 12-B with 20 mole propoxylate of methyl glucoside to be more intense in odor than formula 12-A, 57% could not differentiate between the two and 14.3% chose the 12-A formula without 20 mole propyxylate of methyl glucoside. Thus 85.7% accepted the cologne with 20 mole propoxylate of methyl glucoside as equal to or better than the cologne with the higher concentration of perfume oil. Tests were run on skin. Significant cost savings can be achieved by perfume oil concentration reduction.

EXAMPLE 13—Solvent Pungency in Specially Denatured Alcohol

Specially Denatured Alcohol (U.S. Formula No. 40 with Bitrex denatonium benzoate) was treated with 0.5, 1.0 and 2.0% of 20 mole propoxylate of methyl glucoside. Panelists smelled treated and untreated samples of these alcohols from bottles with openings of 12 and 25 mm and judged them on the relative pungency of the solvent odor. In the material with 2.0% 20 mole propoxylate of methyl glucoside, 100% of the panelists judged the methyl glucoside polyol treated material to be less pungent than and therefore preferred to the untreated SD 40 alcohol. At the 1.0% level of 20 mole propoxylated methyl glucoside, 83% of the panel preferred the methyl glucoside polyol treated material. At the 0.5% level, 67% of the penel preferred the methyl glucoside polyol treated material.

Having set forth the general nature and some specific examples of the present invention, the scope of the invention is now particularly set forth in the appended claims.

I claim:

1. A method of fragrance fixation comprising the addition to a fragrance composition of from about 0.5% to about 5% by weight of the alcoholic, aqueous or hydroalcoholic content of said composition of an alkoxylated methyl glucoside.

2. The method of claim 1 wherein the alkoxylated methyl glucoside is methyl glucoside ethoxylated with from about 5 to about 40 moles of ethylene oxide.

3. The method of claim 1 wherein the alkoxylated methyl glucoside is methyl glucoside propoxylated with from about 5 to about 40 moles of propylene oxide.

* * * * *

UNITED STATES PATENT AND TRADEMARK OFFICE
CERTIFICATE OF CORRECTION

PATENT NO. : 4,264,478
DATED : April 28, 1981
INVENTOR(S) : Abraham Seldner

It is certified that error appears in the above-identified patent and that said Letters Patent are hereby corrected as shown below:

Column 1, line 40, "tives, Among" should read --tives. Among--.

Column 3, line 44, "akaline" should read --alkaline--.

Column 4, line 55, "Toilet" should read --Toilette--.

Column 4, line 59, "8.0" in both occurrences on this line should read --8.0%--.

Column 5, line 61, "Floural" should read --Floral--.

Column 6, line 36, "2.2" should read --2.2%-- and in line 45, "75%" should read --57%--.

Column 7, line 12, "28.5%" should read --28.7%--.

Column 8, line 11, "penel" should read --panel--.

Signed and Sealed this

Eighteenth Day of August 1981

[SEAL]

Attest:

GERALD J. MOSSINGHOFF

*Attesting Officer*     *Commissioner of Patents and Trademarks*